United States Patent [19]

Tamborski et al.

[11] 4,011,267
[45] Mar. 8, 1977

[54] PERFLUOROALKYLETHER SUBSTITUTED ARYL PHOSPHINES AND THEIR SYNTHESIS

[75] Inventors: Christ Tamborski, Dayton; Carl E. Snyder, Jr., Trotwood, both of Ohio

[73] Assignee: The United States of America as represented by the Secretary of the Air Force, Washington, D.C.

[22] Filed: Nov. 6, 1975

[21] Appl. No.: 629,469

[52] U.S. Cl. .................. 260/606.5 P; 252/49.9; 252/389 A; 252/400 A
[51] Int. Cl.[2] ........................ C07F 9/50
[58] Field of Search ............ 260/606.5 P; 252/49.9, 252/389 A, 400 A

[56] References Cited

UNITED STATES PATENTS

| | | | |
|---|---|---|---|
| 3,201,445 | 8/1965 | Drysdale et al. | 252/49.9 X |
| 3,306,855 | 2/1967 | Borecki | 252/49.9 |
| 3,393,151 | 7/1968 | Dolle et al. | 260/606.5 P |
| 3,481,872 | 12/1969 | Dolle et al. | 252/49.9 |
| 3,483,129 | 12/1969 | Dolle et al. | 252/49.9 |
| 3,499,041 | 3/1970 | Tamborski | 260/606.5 P X |
| 3,567,802 | 3/1971 | Garth | 252/49.9 X |

OTHER PUBLICATIONS

Kosolapoff et al., Organic Phosphorus Compounds, Wiley—Intersc. N.Y., vol. 1, pp. 165 and 166 (1972).

*Primary Examiner*—Helen M. S. Sneed
*Attorney, Agent, or Firm*—Joseph E. Rusz; Cedric H. Kuhn

[57] ABSTRACT

Fluorinated phosphines having the following formula:

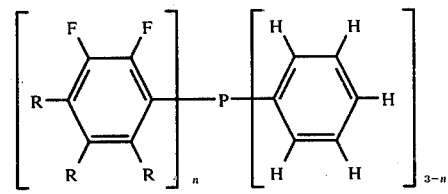

, where R is a perfluoroalkylether group of fluorine with two of the R's being fluorine, and $n$ is 1, 2 or 3. The fluorinated phosphines are especially useful as anticorrosion and antioxidation additives for perfluorinated fluids.

8 Claims, No Drawings

4,011,267

PERFLUOROALKYLETHER SUBSTITUTED ARYL PHOSPHINES AND THEIR SYNTHESIS

RIGHTS OF THE GOVERNMENT

The invention described herein may be manufactured and used by or for the Government of the United States for all governmental purposes without the payment of any royalty.

FIELD OF THE INVENTION

This invention relates to perfluoroalkylether substituted aryl phosphines. In one aspect it relates to a process for synthesizing the phosphines.

BACKGROUND OF THE INVENTION

Because of their thermal stability, perfluorinated fluids have a great potential for use as engine oils, hydraulic fluids and greases. However, a serious drawback in their use results from the fact that certain metals, e.g., certain ones present in aircraft engine components, are corroded by the fluids at temperatures above 550° F in an oxidative environment. In U.S. Pat. No. 3,499,041, issued to one of us on Mar. 3, 1970, certain perfluoroarylphosphines are disclosed that are excellent anticorrosion agents for metals exposed to perfluorinated fluids at 550° F and above in an oxidative environment. While these materials exhibit anticorrosion properties, they have poor solubility at low temperatures and certain members of the class of compounds possess high volatility characteristics for long term high temperature applications. Because of these limitations the compounds are not entirely satisfactory as anticorrosion agents for long term, wide liquid range (−65° F to >600° F) applications.

It is an object of this invention, therefore, to provide improved antioxidation-anticorrosion additives for perfluorinated fluids that are not subject to the above-mentioned limitations.

Another object of the invention is to provide perfluoroalkylether substituted aryl phosphines.

A further object of the invention is to provide a process for synthesizing the phosphines.

Other objects and advantages of the invention will become apparent to those skilled in the art upon consideration of the accompanying disclosure.

SUMMARY OF THE INVENTION

The present invention resides in perfluoroalkylether substituted aryl phosphines (fluorinated phosphines) having the following formula:

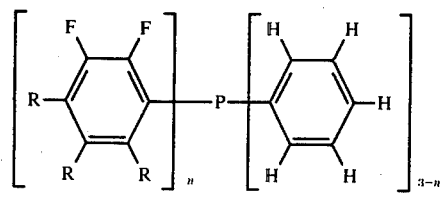

where R is a perfluoroalkylether group ($CF_2R_fOR_f$) or fluorine with two of the R's being fluorine, and $n$ is 1, 2 or 3.

The preferred phosphine compounds are those in which the perfluoroalkylether group is para to the phosphorus atom. In general, R can be any perfluoroalkylether so long as the group contains at least one ether linkage although it is often preferred that the group have two or more ether linkages. Examples of perfluoroalkylether groups (R) include the following:

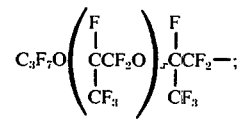

$C_2F_5O(C_2F_4O)_yCF_2CF_2$— and
$CF_3O(CF_2O)_zCF_2CF_2$—, where $x$, $y$ and $z$ are zero or an integer from 1 to 20, inclusive, preferably an integer from 1 to 4, inclusive.

In one embodiment, the present invention resides in a process for preparing the fluorinated phosphines. The procedure followed in preparing completely fluorinated phosphines, i.e., when $n$ in the above formula equals 3, can be represented by the following equations:

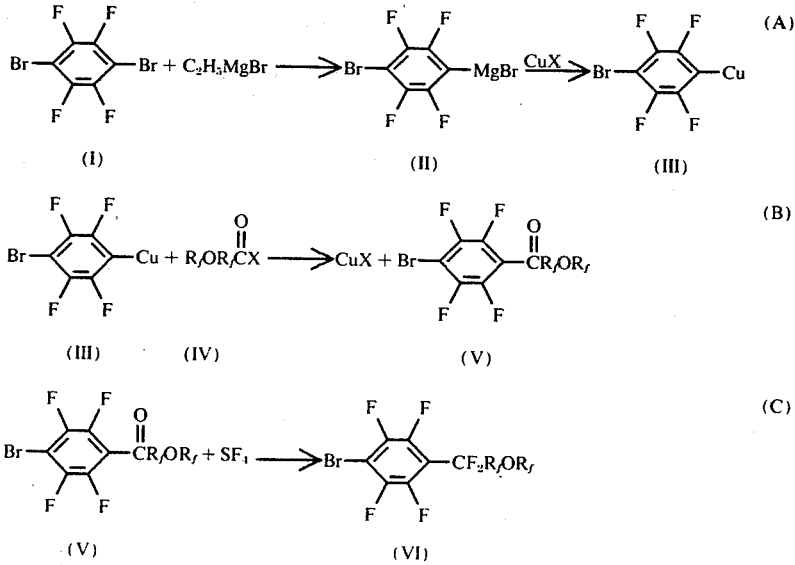

-continued

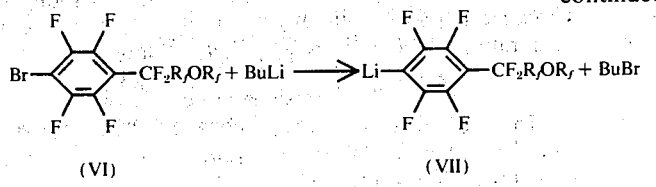

(D)

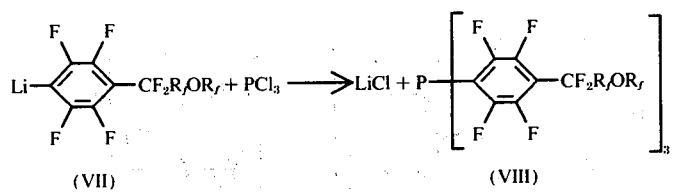

(E)

As seen from equation (A), 1,4-dibromotetrafluorobenzene (I) is reacted with ethylmagnesium bromide. The reaction is carried out by mixing solutions of the compounds in suitable solvents under conditons such as to form compound (II), e.g., at about −5° to 5° C for about 15 minutes to 1 hour. Thereafter, a cuprous halide is added to the reaction mixture whose temperature is then allowed to rise to room temperature. The cuprous halide reacts with compound II, thereby forming the organocopper compound (III).

The organocopper compound is an intermediate which can react with perfluoroacyl halides to yield a variety of ketones. The reaction that occurs is shown by equation (B). In carrying out the described reaction, the perfluroacyl fluoride (IV) is added to the organocopper compound (III) which has been cooled to about −5° to 5° C. The compounds are generally allowed to react at room temperature for a period of about 12 to 24 hours after which the reaction mixture is hydrolyzed. After extracting the mixture with a solvent for the ketone product (V), the solvent layer is phase separated and dried. The ketone is then recovered by fractional distillation.

As shown by equation (C), the ketone is fluorinated by reacting same with sulfur tetrafluoride. This reaction is accomplished by adding anhydrous hydrogen fluoride and sulfur tetrafluoride to a cooled pressure vessel containing the ketone. The sealed pressure vessel is then rocked and maintained at a temperature ranging from about 150° to 200° C for a period of about 12 to 24 hours. After cooling and venting the vessel, the contents are washed with a solvent. The solvent is then evaporated, and the residue is fractionally distilled to yield fluorinate product (VI).

In accordance with equation (D), n-butyllithium is added to a solution of perfluoroalkylether compound (VI) at −70° to −80° C. In the reaction that ensues, which usually takes from 15 minutes to 1 hour, the bromine atom of compound (VI) is replaced with a lithium atom, thereby forming perfluorinated compound (VII). At the end of the reaction period, a solution of phosphorous trichloride is added to compound (VII), and the reaction that occurs yields a phosphine compound (VIII) of this invention. In the reaction as depicted by equation (E), the reaction mixture is stirred at about −70° to −80° C for about 0.5 to 1.5 hours after which it is allowed to warm slowly to about −25° to −35° C over a period of about 3 to 10 hours. Recovery of the product is accomplished by adding dilute hydrochloric acid to the reaction mixture which is phase separated. The bottom viscous layer is washed with water, diluted with hexafluorobenzene and then dried. After filtration and removal of solvent, phosphine product (VIII) is obtained by fractional distillation in the form of a viscous liquid.

The materials that are used in preparing the intermediates and the phosphine products are known compounds that are described in the literature. The foregoing equations illustrate the preparation of the para substitued compounds. However, the present invention is also applicable to the meta and ortho isomers which also function effectively as anticorrosion-antioxidation additives for perfluorinated fluids. In synthesizing the meta and ortho isomers 1,3- and 1,2-dibromotetrafluorobenzene, respectivey, are utilized as a starting material rather than 1,4-dibromotetrafluorobenzene.

Any acyl halide can be used that corresponds to the formula $R_fOR_fC(O)X$, where $R_fOR_f$ is a perfluoroalkylether group and X is a halogen. Examples of suitable acyl halides, which are a source of the $R_fOR_f$ groups, are disclosed in U.S. Pat. Nos. 3,124,599, 3,214,478 and 3,721,696. Thus, depending upon the acyl halide employed, a variety of ketones can be synthesized according to the reaction illustrated by equation (B). As shown by equation (C), the ketone is fluorinated with sulfur tetrafluoride so that its ketone group becomes a $CF_2$ group. Thus, in the above formula defining the flurorinated phosphines of this invention, R equals $CF_2R_fOR_f$ where this group appears in the foregoing equations.

The foregoing description has been concerned with completely fluorinated phosphines. However the present invention is also applicable to partially fluorinated phosphines, i.e., when n in the above formula is 1 or 2. The same procedure as described above is followed except that in the reaction illustrated by equation (E), phenyldichlorophosphine (n=2) or diphenylchlorophosphine (n=1) is reacted with compound (VII) instead of phosphorous trichloride. The reactions involved can be represented by the following equation:

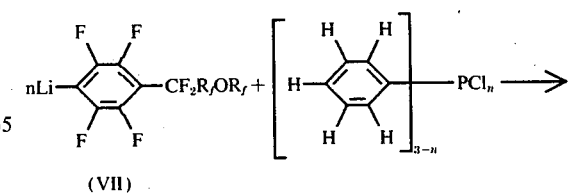

-continued

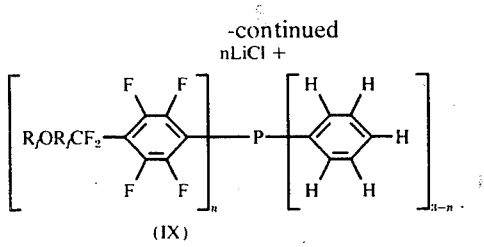

In equation (F), n equals 1 or 2.

A more complete understanding of the invention can be obtained by referring to the following illustrative examples which are not intended, however, to be unduly limitative of the invention. In the examples, the Roman numerals refer to compounds so designated in the foregoing equations.

EXAMPLE I

Synthesis of

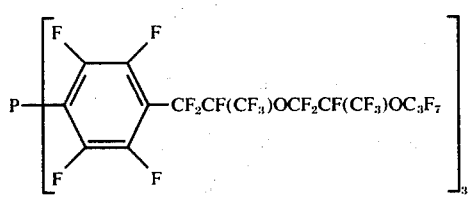

To a solution of 1,4-dibromotetrafluorobenzene (I) (30.8 g, 0.100 moles) in anhydrous tetrahydrofuran (250 ml) at 0° C, ethylmagnesium bromide (61.7 ml of a 1.62 M diethyl ether solution) was slowly added. After the solution was stirred for approximately 0.5 hour at 0° C, cuprous chloride (12.5 g, 0.125 moles) was added. Stirring was continued while the reaction mixture was allowed to rise to room temperature. To this organocopper intermediate (III) cooled to 0° C, the perfluoroacyl fluoride (IV) [where $R_fOR_f$ = $C_3F_7OCF(CF_3)CF_2OCF(CF_3)$] (49.8 g, 0.100 moles) was slowly added. The reaction mixture was stirred at room temperature for 15 hours. The resulting brown mixture was hydrolyzed with 2N. HCl (100 ml). The mixture was extracted three times with diethyl ether (600 ml total). The diethyl ether layer was phase separated and dried (MgSO$_4$). Distillation yielded the ketone (V), b.p. 248°–251° C, yield 65.5%.

Nuclear magnetic resonance and infrared analysis were consistent with the proposed structure. Elemental analysis of compound (V) for the structure

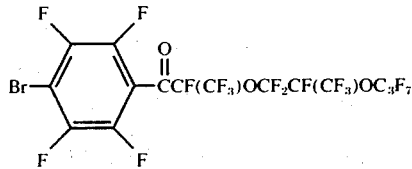

gave the following indicated results.

Calculated: C, 25.49; H, 0.00; Br, 11.25; Found: C, 25.20; H, 0.00; Br, 11.36

Mass Spectral Analysis:

M. W. Calculated, 707;
Found, 707.

The ketone (V) (34.7 g, 0.0514 mole) was placed into a 300 ml Monel pressure vessel. The vessel was cooled in a Dry Ice bath while anhydrous hydrogen fluoride (9.2 g, 0.46 mole) and sulfur tetrafluoride (24.8 g, 0.23 mole) were added. The pressure vessel was sealed, rocked and heated to 180° C for 18 hours. The vessel was cooled, vented and the contents were washed with diethyl ether. The solvent was evaporated and the residue was fractionally distilled to yield the fluorinated product (VI), b.p. 76° C/2 mm, in 68% yield. Nuclear magnetic resonance and infrared analysis were consistent with the proposed structure. Elemental analysis of compound (VI) for the structure

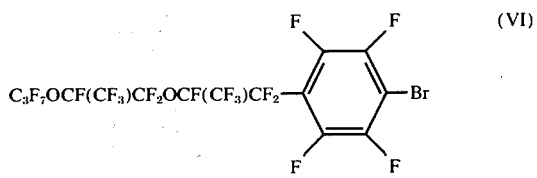

gave the following indicated results.

Calculated: C, 24.72; H, 0.00; Br, 10.91; Found: C, 24,81; H, 0.00; Br, 10.5.

Mass Spectral Analysis:

M. W. Calculated, 729;
Found, 729.

To a diethylether (50 ml) — tetrahydrofuran (60 ml) solution of the perfluoroalkylether compound (VI) (10.94 g, 0.015 mole) at −78° C was slowly added n-butyllithium (9.4 ml of 1.6 M hexane solution, 0.015 mole). After 30 minutes a diethylether solution (10 ml) of phosphorous trichloride (0.6 g, 0.0044 mole) was added. The reaction was stirred at −78° C for 1 hour and allowed to warm slowly to −30° C in 5 hours. Dilute hydrochloric acid (10 ml, 6 N) was added and the reaction was stirred for 30 minutes. The mixture was phase separated and the bottom viscous layer was washed repeatedly with water. The organic layer was diluted with hexafluorobenzene (15 ml) and dried (MgSO$_4$). After filtration and removal of solvent, the product was distilled to yield a viscous liquid product (VIII), b.p. 200° C/0.005 mm, in 50% yield. Nuclear magnetic resonance and infrared analysis were consistent with the structure. Elemental analysis of compound (VIII) for the structure

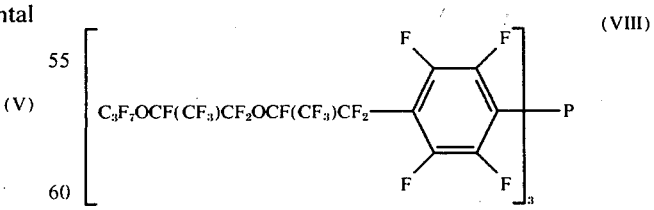

gave the following indicated results.

Calculated: C, 27,31; H, 0.00; Found: C, 27.33; H, 0.00.

EXAMPLE II

Synthesis of the partially fluorinated phosphine

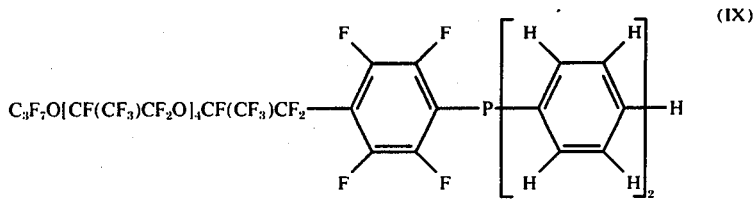

To a solution of

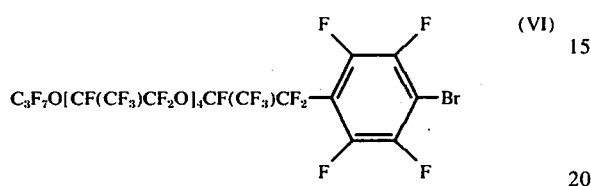

(24.5 g, 0.02 moles) in anhydrous tetrahydrofuran (175 ml) and anhydrous diethylether (100 ml) at −78° C, n-butyllithium (15.4 ml. of 1.3 M hexane solution, 0.020 mole) was added. After approximately 1 hour, a diethylether (100 ml) solution of diphenylchlorophosphine (4.25 g, 0.019 mole) was added at −78° C. The reaction was stirred at this temperature for approximately 15 hours, allowed to reach room temperature and stirred for an additional 15 hours. The reaction was hydrolyzed with 6 N hydrochloric acid, phase separated, dried and distilled under reduced pressure to yield a viscous liquid product (IX), b.p. 148° C/0.005 mm in approximately 50% yield. Nuclear magnetic resonance and infrared analysis were consistent with the structure. Elemental analysis of compound (IX) for the structure,

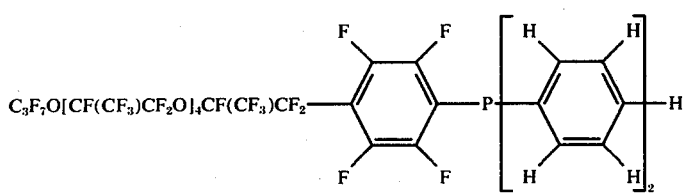

gave the below-indicated results.

Calculated: C, 32.45; H, 0.76; Found: C, 32.20; H, 0.86.

Mass Spectral analysis
M. W. Calculated, 1332;
Found, 1332.

EXAMPLE III

A series of runs was conducted in which the procedure described in Example I was followed in preparing fluorinated phosphines of this invention. The perfluoroacyl fluorides (IV) used in Example I, were employed in which $R_fOR_f$ was as follows:
 (a) $C_3F_7OCF(CF_3)$—
 (b) $C_2F_5O(C_2F_4O)_2CF_2$—
 (c) $CF_3O(CF_2O)_3CF_2$—
 (d) $C_3F_7O[CF(CF_3)CF_2O]_4$—$CF(CF_3)$—

The products obtained in the runs were fluorinated phosphines having the following formulae:

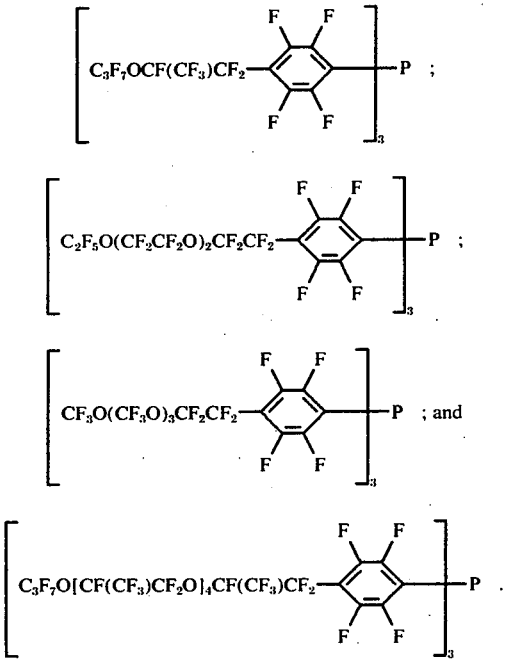

Incorporation of the fluoroinated phosphines of this invention in perfluoroalkylether fluids, e.g., fluids of the type disclosed in U.S. Pat. No. 3,393,151, inhibits the oxidation-corrosion of various metals with which the fluids come into contact. In general, only small amounts of the additives are required, e.g., about 0.05 to 5.0 percent by weight of the base fluid. Furthermore, the additives prevent the decomposition of the fluids when exposed to a high temperature (500°–650° F) oxidation environment in the presence of metals. Of primary importance the fluorinated phosphines exhibit better low temperature solubility and lower volatility than the prior art perfluoroarylphosphines.

As will be evident to those skilled in the art, modifications of the present invention can be made by those skilled in the art without departing from the spirit and scope of the invention.

We claim:

1. A fluorinated phosphine having the following formula:

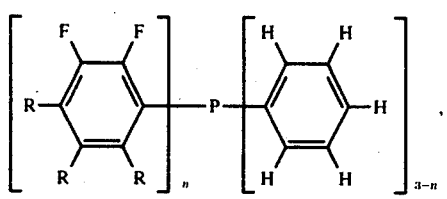

where one of the R's is a perfluoroalkylether group, two of the R's are fluorine, and $n$ is 1, 2 or 3.

2. The fluorinated phosphine of claim 1 in which the perfluoroalkylether group is

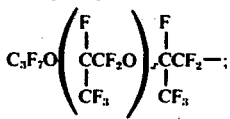

$C_2F_5O(C_2F_4O)_yCF_2CF_2-$;

or $CF_3O(CF_2O)_zCF_2CF_2-$;

where $x$, $y$ and $z$ is zero or an integer from 1 to 20 inclusive.

3. The fluorinated phosphine of claim 2 in which the perfluoroalkylether group is $C_3F_7OCF(CF_3)CF_2-$ and $n$ is 3.

4. The fluorinated phosphine of claim 2 in which the perfluoroalkylether group is $C_3F_7OCF(CF_3)CF_2OCF(CF_3)CF_2-$ and $n$ is 3.

5. The fluorinated phosphine of claim 2 in which the perfluoroalkylether group is $C_3F_7O[CF(CF_3)CF_2O]_4CF(CF_3)CF_2-$ and $n$ is 3.

6. The fluorinated phosphine of claim 2 in which the perfluoroalkylether group is $C_2F_5O(C_2F_4O)_2CF_2CF_2-$ and $n$ is 3.

7. The fluorinated phosphine of claim 2 in which the perfluoroalkylether group is $CF_3O(CF_2O)_3CF_2CF_2-$ and $n$ is 3.

8. The fluorinated phosphine of claim 2 in which the perfluoroalkylether group is $C_3F_7O[CF(CF_3)CF_2O]_4CF(CF_3)CF_2-$ and $n$ is 1.